United States Patent [19]

Percarpio

[11] 4,106,497
[45] Aug. 15, 1978

[54] MULTIPLE SAMPLE NEEDLE ASSEMBLY WITH INDICATOR MEANS

[75] Inventor: Edward P. Percarpio, North Haledon, N.J.

[73] Assignee: Becton, Dickinson and Company, East Rutherford, N.J.

[21] Appl. No.: 765,868

[22] Filed: Feb. 4, 1977

[51] Int. Cl.[2] .............................................. A61M 5/00
[52] U.S. Cl. ............................... 128/2 F; 128/DIG. 5
[58] Field of Search ................ 128/2 F, DIG. 5, 276, 128/214 R, 214 B, 215, 220, 218 NV

[56] References Cited

U.S. PATENT DOCUMENTS

| 3,734,080 | 5/1973 | Petterson et al. | 128/2 F |
|---|---|---|---|
| 3,817,240 | 6/1974 | Ayres | 128/2 F |
| 3,874,367 | 4/1975 | Ayres | 128/2 F |
| 3,886,930 | 6/1975 | Ryan | 128/2 F |

*Primary Examiner*—John D. Yasko

*Attorney, Agent, or Firm*—Kane, Dalsimer, Kane, Sullivan & Kurucz

[57] ABSTRACT

Apparatus for collecting blood samples from a patient. The apparatus includes a housing. A first hollow, pointed needle extends forwardly from the housing and is adapted to pierce the tissues of a patient and conduct blood therefrom. A blood flow indicator is coupled with the first needle and is adapted to provide a visual signal when the needle has penetrated a blood vessel. A chamber in the housing is in fluid communication with a normally closed valve adapted when closed to prevent any fluid from flowing out of the chamber. A second hollow pointed needle extends rearwardly from the housing. The valve is adapted to be activated and shifted from the normally closed position to an open position to prevent flow of blood from the patient to a blood container. The blood flow indicator includes a control to provide for a limited amount of blood to be directed to a predetermined location for indication purposes and to isolate the limited amount of blood and to prevent leakage beyond the desired location.

15 Claims, 9 Drawing Figures

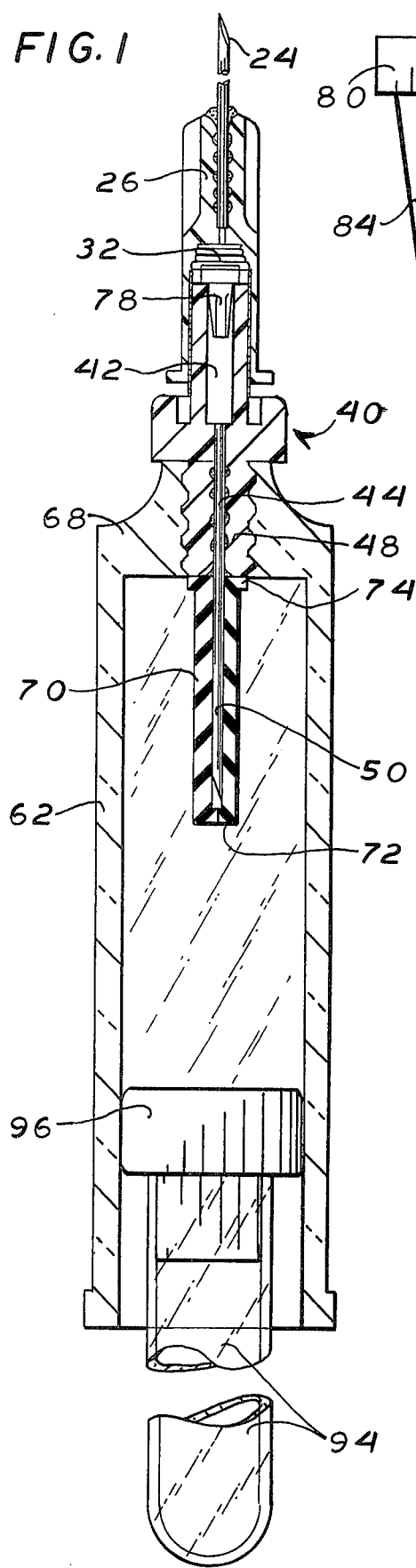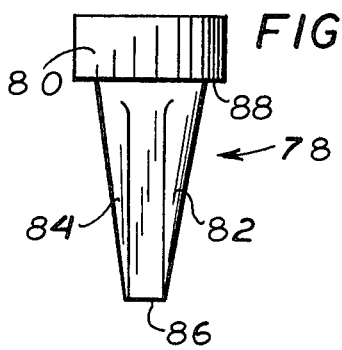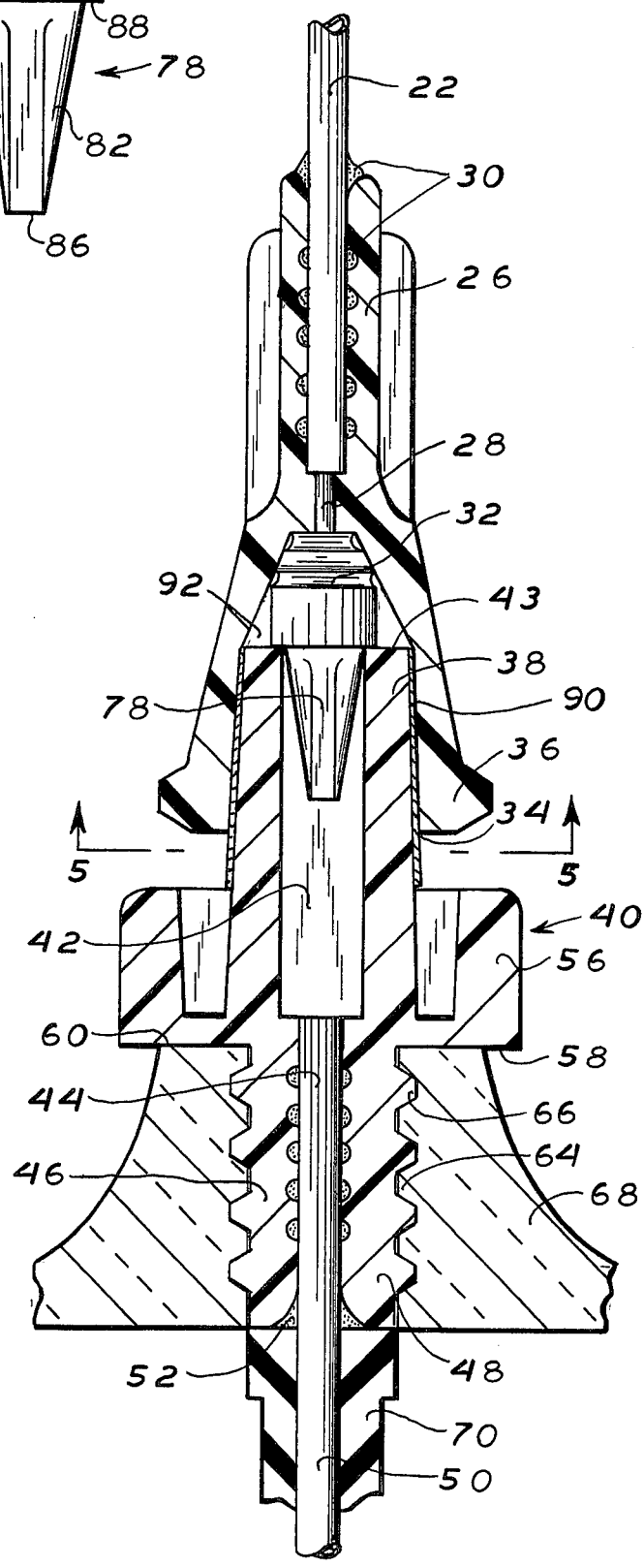

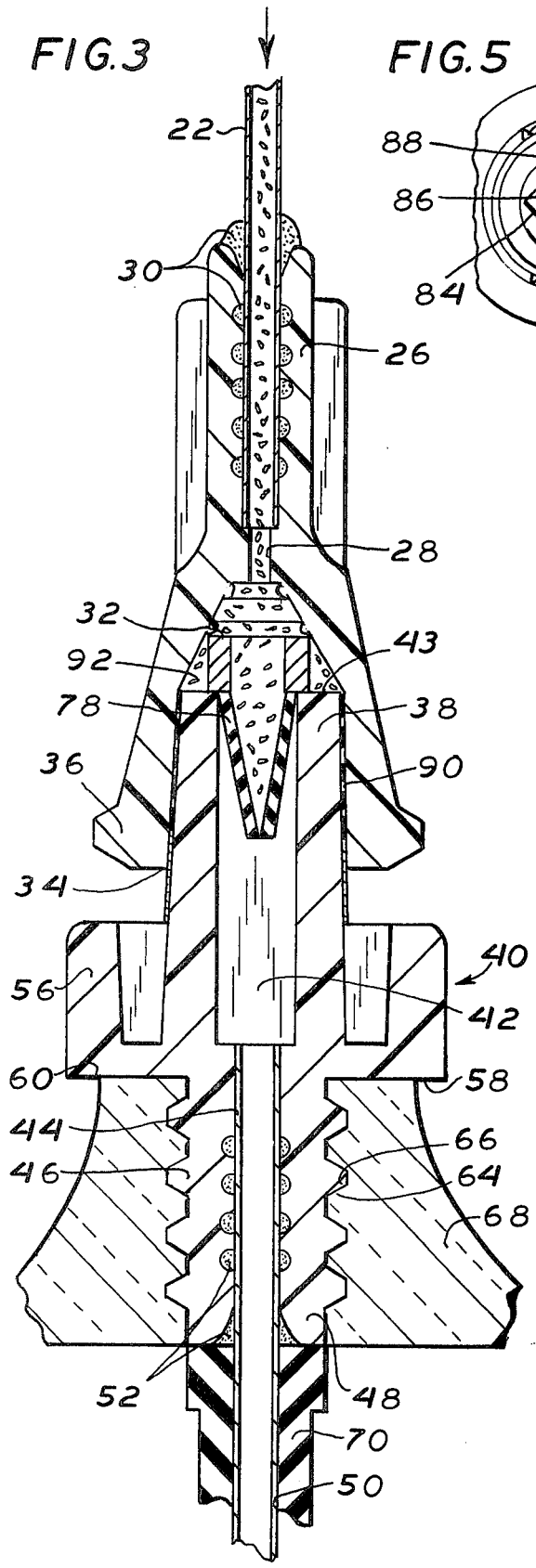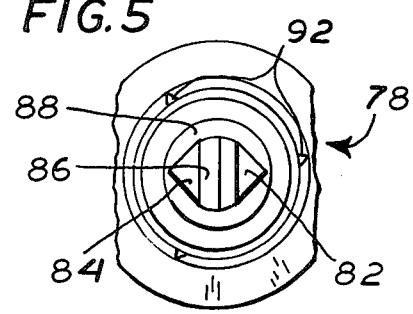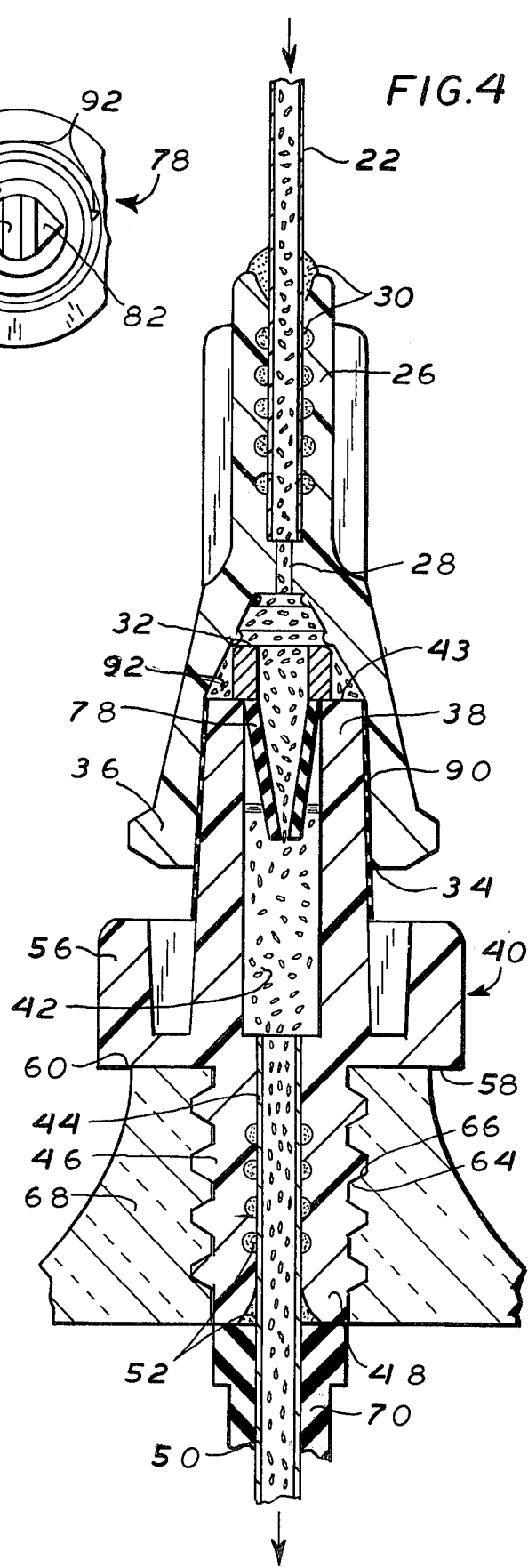

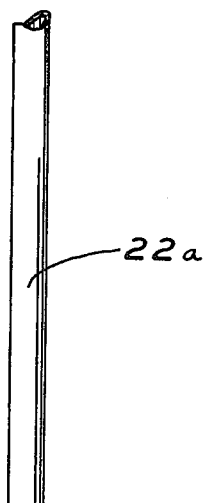
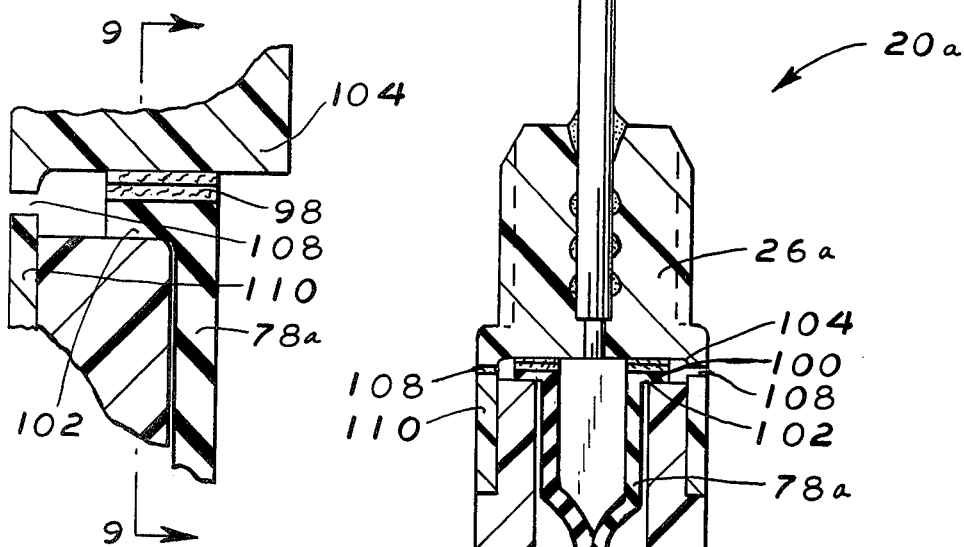
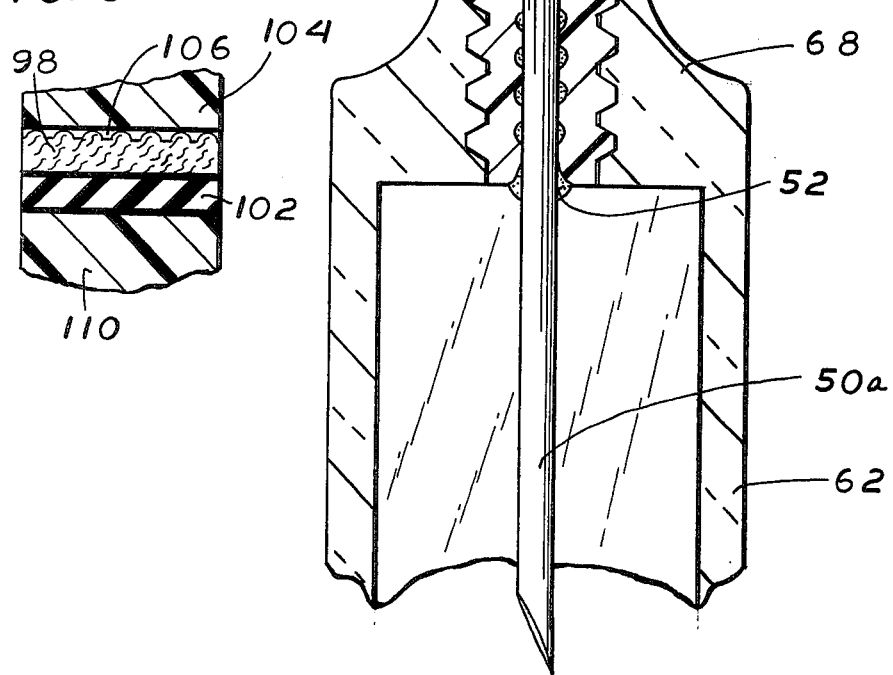

MULTIPLE SAMPLE NEEDLE ASSEMBLY WITH INDICATOR MEANS

BACKGROUND OF THE INVENTION

There are many different types of devices and apparatus systems presently available on the market for collecting single and multiple samples of blood in one or more different containers with only a single entry into the tissues of the patient. The many different types of structures are designed to operate in a variety of different ways and to achieve a variety of different effects. Valve structures are employed to shut off blood flow automatically as the evacuated containers are interchanged for successive samples. Furthermore, various types of check valve devices are also employed to permit flow of blood from the patient to a container and to automatically close and prevent back flow of blood or other fluids such as medicaments in the evacuated containers to the patient. Additionally with the many different types of valve structures, there are also many different types of indicators employed to indicate when a veni-puncture has been achieved and blood has entered the device so that the device can be coupled to an evacuated container to draw blood therethrough from the patient. The various types of indicators are designed to provide a showing of blood to the operator so that he is assured that veni-puncture has been achieved and it is the proper time to interconnect the evacuated container tube with the system and draw blood into the tube. Actually the indicator which shows blood to the operator indicating veni-puncture should not be leaked from the device so that contamination of the operator or the surrounding area occurs. An example of a patented system which employs the above features is present in U.S. Pat. No. 3,817,240.

Naturally it is always advantageous to provide additional improvements to the overall blood collecting system particularly in the use of valving mechanism for collection and anti-back flow consideration as well as providing an indicator which is positive acting and dependable and which detracts as little as possible from the actual operation of the collecting system while giving effective and positive indication of veni-puncture without the danger of contamination.

SUMMARY OF THE INVENTION

It is among the primary objectives of the present invention to provide a blood sample needle assembly for single or multiple sampling purposes which effectively provides a check valve structure to guard against back flow into the patient during the sampling process, and which provides an indicator to effectively signal a proper veni-puncture without permitting contamination of the blood being collected or of the surrounding area due to blood leakage. With the appropriate signal, evacuated container for collecting a sample can be coupled with the remainder of the system and blood will flow from the patient into the container.

The system is designed to be disposable since it is inexpensive to manufacture, store and use. The indicator is designed so that it is adapted to be positioned at a location where it will be activated upon successful puncture of a patient's vein to collect and capture a portion of blood visible to the operator thereby indicating the successful veni-puncture. The system is designed so that the back flow prevention valve and the indicator can be utilized in a single blood sample assembly or a multiple blood sample assembly.

In summary, apparatus is provided for collecting blood samples from a patient. The apparatus includes a housing. A first hollow, pointed needle extends forwardly from the housing and is adapted to pierce the tissues of a patient and conduct blood therefrom. Blood flow indicating means is coupled with the first needle and is adapted to provide a visual signal when the needle has penetrated a blood vessel. A chamber in the housing is in fluid communication with a normally closed valve means adapted when closed to prevent any fluids from flowing out of said chamber. A second hollow pointed needle extends rearwardly from the housing. The valve means is adapted to be activated and shifted from the normally closed position to an open position to permit flow of blood from the patient to a blood container. The blood flow indicating means includes control means to provide for a limited amount of blood to be directed to a predetermed location for indication purposes and to isolate the limited amount of blood and to prevent leakage beyond the desired location.

With the above objectives among others in mind, reference is made to the attached drawings.

BRIEF DESCRIPTION OF THE DRAWINGS

FIG. 1 is a longitudinal sectional view of the apparatus of the invention with a fragmentary portion of an evacuated collection container in partial association therewith and a fragmentary portion of the veni-puncture needle depicted;

FIG. 2 is an enlarged fragmentary sectional view thereof prior to veni-puncture.

FIG. 3 is an enlarged fragmentary sectional view thereof subsequent to veni-puncture with arrows showing the flow of blood for indicating purposes;

FIG. 4 is an enlarged fragmentary sectional view thereof subsequent to coupling with an evacuated collection container with arrows showing the flow of blood into the container for collection;

FIG. 5 is a cross sectional view thereof taken along the plane of line 5—5 of FIG. 2;

FIG. 6 is a side elevation view of the check valve portion of the invention;

FIG. 7 is an enlarged fragmentary sectional view of an alternative embodiment of the invention subsequent to veni-puncture with arrows showing the flow of blood for indicating purposes;

FIG. 8 is an enlarged fragmentary sectional view thereof showing the location of the indicator means; and FIG. 9 is a fragmentary enlarged sectional view thereof taken along the plane of line 9—9 of FIG. 8.

DESCRIPTION OF THE PREFERRED EMBODIMENTS

The multiple needle assembly apparatus as shown in FIGS. 1–6 includes a forward veni-puncture needle 22 having a pointed end 24 for penetration into a blood vessel of a patient. The rear end portion of needle 22 is mounted in a hub 26 having a continuous passageway 28 therethrough. The needle is mounted in the forward end of passageway 28 by means of epoxy 30. Naturally other conventional mounting means is acceptable.

Passageway 28 widens a short distance beyond the rear end of needle 22 to form a chamber 32. The rear end of the hub has an opening 34 communicating with the remainder of passage 28 and has a conventional peripheral rim 36. The opening from chamber 32 to the rear open end 34 of hub 26 tapers outwardly to facilitate reception of the fustroconical forward end portion 38 of adapter member 40. Forward fustroconical end 38 has a central passageway 42 therethrough open at the forward end for communication with chamber 32. The forward edge 43 of fustroconical portion 38 forms a boundary for chamber 32 along with the cooperating adjoining surfaces of the inner portion of hub 28.

Opening 42 through fustroconical portion 38 continues in communication with a narrower opening 44 in the rear end portion 46 of adapter 40. Opening 44 extends to the rear end 48 of the adapter 40 and is open so that a second pointed needle 50 can be inserted into opening 44 and bonded in place by means of epoxy 52 or other convenient fastening means. Naturally both needles 22 and 50 are hollow so as to provide a continuous passageway through the interconnected assembly by means of communication between the opening through needle 22, passageway 28, chamber 32, passageway 42, the hollow opening in needle 50 mounted in passageway 44 and the pointed rear end 54 of needle 50.

The rear end of fustroconical portion 38 of adapter 40 includes an annular skirt 56 having a shoulder 58 on its under surface for mating interengagement with the front rim 60 of an evacuated tube holder 62. Furthermore, the rear end portion 46 of adapter 40 has a threaded outer surface 64 for interengagement with a threaded through passageway 66 in the forward reduced neck portion 68 of holder 62. Consequently, holder 62 can be coupled with adapter 40 and accordingly, apparatus 20 by means of threadedly interengaging rear portion 46 with the holder 62 until under surface 58 of skirt 56 seats on the forward rim 60 of the holder.

The exposed end portion of needle 50 which extends beyond the rear edge 48 of adapter 40 is surrounded or capped by a resilient, self-sealing elestomeric sleeve 70 of a conventional material such as natural or synthetic rubber. Cap 70 which has a closed puncturable rear end 72 is open at its forward end to receive the needle therein and has an annular flanged end 74 opposite to the closed end which seats against the rear edge 48 of adapter 40. The dimensions of the sleeve or cap positioned on the needle is small enough so that it can be inserted through the threaded opening in holder 62 when threaded interengagement is achieved between the adapter 40 and the holder 62 with the result being that the capped end of needle 50 is located within the hollow interior 76 of holder 62. Cooperating surfaces between needle 50, adapter 40, and sleeve 70 form a valve means which operates automatically when coupling and uncoupling of a tube 94 and stopper 96 therewith. This automatic valve is optionally utilized when the assembly is designed for taking multiple samples of blood with a single veni-puncture. Alternatively, check valve 78 will perform the function of closing off the flow whenever an evacuated blood-collection tube is not connected to the fluid path.

Mounted interiorally of the sampling device is a check valve 79 which is of a similar material as sleeve 70. The check valve has a cylindrical hollow base portion 80 with a pair of tapered opposing flaps 82 and 84 extending rearwardly therefrom in engagement in the normal relaxed position so as to seal one end of the opening through the valve extending from the opening in the base portion 80. The portions of flaps 82 and 84 opposite to the adjacent engaging walls have a triangular shaped enlarged configuration tapered inwardly toward the rear end 86 of the valve to reinforce the flaps and facilitate operation of the check valve.

Flap portions 82 and 84 terminate in engagement with the base 80 at a point inward of the outer diameter of the base so as to form a circular shoulder 88. This shoulder 88 forms a seating surface for the check valve 78 on the forward rim 43 of adapter 40. Passageway 42 in the forward portion 38 of adapter 49 is large enough to receive flaps 84 and 82 therein. The flaps 82 and 84 in the relaxed position have their inner walls in engagement thereby sealing the opening therethrough with the opening in base portion 80 in communication with chamber 32.

Surrounding the outer surface of forward portion 38 of adapter 40 is a film of water expansible material 90 initially in the dry condition and therefore unexpanded. Three spaced channels 92 are formed in the film to provide air passageways for facilitating venting of the assembly and flow of blood into the indicator area where film 90 is located. The number of channels is a matter of choice. Thereafter, expansion of the film due to contact with the liquid closes channels 92 and locks the blood into the area of the location of the film and prevents leakage beyond the rear flanged end 36 of hub 26. The walls of hub 26 surrounding the film 90 are transparent or translucent so that the blood captured by the film and indicating a successful veni-puncture is observable by the operator. The expansion of the film to close off the channels prevents leakage of the blood beyond the rear end of the hub and eliminates the danger of possible contamination of the surrounding area including the operator. Furthermore, by capturing the blood within the indicator area including channels 92, there is no danger of contamination of blood being collected into chamber 32 and ultimately into an evacuated container through the passageway interconnected with rear needle 50.

Materials for the various components are of a conventional low cost nature adapted for mass production and disposability. Hub 26 and adapter 40 can be of a conventional metal or plastic material and it is particularly useful if the portion of hub 26 surrounding the indicator film 90 is transparent or at least translucent to permit observability of blood collected between the adapter and hub in the indicator area.

The holder 62 can be of a glass or plastic material of a conventional nature and, as described above, the check valve 78 can be of a conventional resilient self-sealing material such as a natural or synthetic rubber which is also true of the rear sleeve or cap 70 which forms part of the valve assembly with the rear portion of needle 50.

The evacuated tube 94 is also of a conventional material such as glass and contains a conventional self-sealing, puncturable stopper 96 maintaining the vacuum within the tube 94 and adapted to be pierced by the rear pointed end of needle 50 to subject the apparatus 20 to the vacuum for blood collection. The size of stopper 96 and tube 94 is such that it is guided by the interior walls of holder 62 into proper alignment and interengagement with the needle 50 for blood collection purposes.

In operation, assembly 20 is interconnected with a holder 62 as depicted in FIG. 1 with the threaded interengagement being achieved between portion 46 of the adapter and the threaded forward surface of holder 62. A tube 94 for blood collection is positioned in the rear end of holder 62 in alignment for coupling with the assembly 20 as depicted in FIG. 1. In this position, both the check valve 78 and the valve assembly formed by sleeve 70, needle 50 and the adapter are in the normal closed position. The water expansible material is in the unexpanded condition as shown in FIG. 2 with the appropriate channels 92 in the film providing air passageways for communication between chamber 32 and the atmosphere at the rear flanged end 36 of hub 26.

Veni-puncture is then accomplished by inserting point 24 of needle 22 into the patient and into a blood vessel causing blood to flow through the needle and passageway 28 into chamber 32 and into the central opening 98 within valve 78. However, the terminal inward end of the valve represented by interengaging flaps 82 and 84 is closed so that the blood can flow no further. This condition is depicted in FIG. 3 of the drawings. Blood is permitted to flow through channels 92 in the film 90 until the water expansible material forming the film expands sufficiently to close the channels 92 and stop the blood flow. However, the travel of blood along the channels is observable through the walls of hub 26 thereby indicating the presence of a successful veni-puncture. Further travel of the blood is prohibited and the blood is sealed within the channels thereby preventing contamination of the area surrounding assembly 20 or the possibility of blood returning in contaminated form into the main blood flow within chamber 32.

Tube 94 is then advanced in holder 62 until the pointed end 54 of needle 50 pierces the stopper 96 and enters the evacuated tube. This is accomplished in conventional fashion with sleeve 70 being collapsed about needle 50 with the needle piercing both the sleeve 70 and the stopper 96. The difference in pressure caused by the vacuum within tube 94 causes the flaps of check valve 82 and 84 to separate permitting flow of blood through the check valve 78 and through passageway 42 and communicating needle 50 into the evacuated tube 94 for blood collection purposes. Any danger of low in the opposite direction due to a condition which causes a pressure build up and back flow will cause the flaps 82 and 84 to be closed against one another sealing the check valve and thereby preventing back flow into chamber 32 and ultimately through needle 22 into the patient. The flow path for blood collection in this manner is depicted in FIG. 4 of the drawings.

Thereafter, the evacuated tube 94 and stopper 96 are removed from needle 50 permitting the resilient self-sealing cap or sleeve 70 to return to its relaxed position covering and sealing the end 54 of needle 50 and preventing further flow therethrough. This prevents leakage of blood into the holder 62. At the same time, with the equalization of pressure flaps 82 and 84 will return to the relaxed condition in sealing interengagement. Any back flow condition that may occur will naturally continue to tend to close check valve 78 forcing flaps 82 and 84 into tighter interengagement. This can occur due to equalization of pressure within the system since the source of vacuum has been removed or due to a back pressure condition. In this manner the danger of blood flow back into the patient is eliminated.

The collection process can then be repeated for as many samples as desired with the operator merely coupling a further tube and stopper to the needle 50 within the holder and creating the pressure differential to permit blood to flow through the system into the container. This is accomplished without the necessity of removal of needle 22 from the patient or any additional requirement for a further veni-puncture.

Of significance is the formation of the indicator means which permits air to be bled into the system so that blood can fill a predetermined controlled area where it can be observed to indicate a successful veni-puncture. Thereafter, the fluid which is permitted to enter the predetermined chamber is automatically sealed off in that area so that it does not leak or possibly contaminate either the surrounding area or return to the collection system in a manner where possible contamination could occur. The means for achieving this result lies in the provision of a water expansible material located in a specific area and a plurality of channels which will facilitate introduction of a fluid such as blood into the predetermined area and then the water expansible material will automatically seal that area off. The material can be in the form of a film or tape mounted on the adpater or, alternatively, it can be in the form of a powder positioned in the space between the adapter and the hub in place of the film. For example, a sodium alginate powder which is of tan color and is medium coarse like salt can be employed or polyvinylpyrolidone powder which is a white very fine powder can also be employed. A further suggested material would be an SGP-502 powder which is also tan and it has a coarseness intermediate the above two mentioned powders. All three powders absorb a water or blood droplet very quickly and would be acceptable for the water expansible material of the present invention. The powder would be sprinkled on the adapter surface the predetermined location for the film and the adapter would than be coupled with the hub as depicted. The powder provides a space for an air bleed between the particles, but when the liquid water or blood tries to travel between the needle hub and adapter interface the powder will expand by becoming saturated and block off further leakage locking the blood in position for viewing through the hub by the operator. The air path is between the particles of the powder and when the powder expands the air path or air bleed is cut off and fluid flow of blood naturally stops. The film 90 is formed of powders of the above discussed type or similar powders and is adaptable for channels to be cut therein for the necessary air bleeding function to permit the flow of blood into the channels prior to expansion thereof. Thus when the liquid attempts to follow the air out the channels, the film would swell and expand to form a tight seal locking the blood in position and indicating a veni-puncture.

An alternative embodiment is depicted in FIGS. 7-9 and includes identical components as the previously discussed embodiments for the most part and like numbers are utilized for these components bearing the additional subscrip a. The areas of difference reside in the nature of the positioning of the indicator means and the fact that a sleeve corresponding to sleeve 70 is not present on needle 50a additionally, check valve 78a has a slightly different configuration but operates in the same manner in permitting blood to flow through the assembly and closing when back flow conditions exist. In this alternative embodiment the water expansible indicator material 98 is located between the upper surface 100 formed on the flanged end 102 of check valve 78a and the undersurface 104 of hub portion 26a. The water expansible material 98 includes a plurality of channels 106 extending laterally of the assembly and communicating with a series of vent holes 108 through a transparent portion 110 of hub 26a. The vent holes 108 and channels 106 in communication provide a vent for air to pass between the atmosphere and the interior of the assembly so that blood will flow when a veni-puncture is accomplished and inter channels 106 whereupon the water expansible material 98 will expand and lock the blood in position. The locked blood is then visible to the transparent walls 110 indicating a successful veni-puncture. The operation of the water expansible material 98 is identical as in the previously discussed embodiment and can be made of the same materials discussed in connection with that embodiment.

The assembly of FIGS. 7-9 is designed for single sample use due to the fact that a valve assembly including a sleeve similar to sleeve 70 has not been included on needle 50a. Alternatively, the sleeve could be included and the assembly 20a of FIGS. 7-9 could be used for multiple sampling of blood in the same manner as discussed in connection with the embodiment of FIGS. 1-6. Conversely, the embodiment of 1-6 can be used for single sample use in which case sleeve 70 would not be employed.

In single sampling, the pointed end of needle 22a is inserted into the vein after stopper 96 of the evacuated tube 94 has been partially inserted onto the pointed end of needle 50a. However the needle 50a is not inserted fully through the stopper so that there is no communication with the vacuum conditions within the tube. Once the veni-puncture has been accomplished, blood will flow through needle 22a, through passageway 28a and into the channels 106 where it will be sealed by expanding material 98. The operator than observes the indicating blood through transparent housing 110 and completes coupling of tube 94 with needle 50a by passing the pointed end of needle 50a fully through stopper 96 and into communication with the evacuated tube. The difference in pressure will then cause check valve 78a to open and blood will be collected in the tube. As in the previous embodiment when the flow blood sample has been collected, the equalization of pressure will permit check valve 78a to return to its initial configuration closing off the flow path. Additionally, any back flow stages will be eliminated by the fact that check valve 78a will close automatically with sufficient pressure applied from the end opposite to the veni-puncture end. When the single sample has been collected, the entire assembly is removed from the patient, thus eliminating the necessity of the valve assembly to close off the needle while containers are changes as is required with multiple sampling.

Thus several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. Apparatus for collecting blood samples from a patient comprising:
a housing;
a first hollow, pointed needle extending forwardly from the housing and adapted for piercing the tissues of a patient and conducting blood therefrom;
blood flow indicating means coupled with said first needle and adapted to provide a visual signal when the sample has penetrated a blood vessel;
a chamber in the housing in fluid communication with a normally closed valve means adapted when closed to prevent any blood from flowing out of said chamber;
a second hollow pointed needle extending rearwardly from the housing;
said valve means adapted to be activated and shifted from the normally closed position to an open position to permit flow of blood from the patient to a blood sample container;
said blood flow indicating means including control means to provide for a limited amount of blood to be directed to a predetermined location for indication purposes and to isolate the limited amount of blood and to prevent leakage beyond the desired location including means facilitating the prevention of collection of the limited amount of blood with the blood sample accumulated in the container.

2. The invention in accordance with claim 1 wherein said valve means includes a normally closed first valve positioned with respect to said second hollow pointed needle to cooperate with a blood container coupled with the needle so as to be automatically activated and shifted from the normally closed position to an open position to permit flow of blood from the patient to the blood container and to automatically return to the normally closed position when the blood container is uncoupled, then to operate in the same manner with as many other prescribed containers as desired with a single penetration of the patient to collect a series of blood samples in a successive containers without blood spillage while changing containers, a check valve coupled with the first needle and adapted to assume a first position to enable blood to flow out of the patient and a second position to prevent any fluid from flowing back into the patient.

3. The invention in accordance with claim 1 wherein the valve means includes a check valve coupled with said first needle and adapted to assume a first position to enable blood to flow out of the patient into a container and a second position to prevent any fluid from flowing back into the patient.

4. The invention in accordance with claim 1 wherein the control means includes at least one passageway in the housing in communication with the chamber and including sealing means therein so that upon accumulation of blood in the chamber and entrance into the passageway the sealing means will become activated to seal the passageway and prevent the blood from flowing therethrough beyond a predetermined location and the housing surrounding the passageway being of a material to permit visual observation of the blood flowing into and sealed in the passageway.

5. The invention in accordance with claim 2 wherein the first valve means includes an elastomeric sleeve mounted in surrounding engagement with the second hollow pointed needle and normally closing the opening to the second hollow pointed needle and being of a resilient self-sealing elastomeric material so as to be adapted to be automatically shifted to a collapsed position exposing the opening in the needle and permitting blood to flow through the opening therein and when released to automatically return to the initial configuration closing and sealing the opening in the second hollow pointed needle.

6. The invention in accordance with claim 2 wherein a blood container is provided with a resilient closure maintaining a partial vacuum in the container, so positioned and arranged that when the container is pushed forward and resilient closure automatically opens the first valve means and causes the second pointed needle means to penetrate through the resilient closure thereby enabling the patient's blood to flow into the container and when the container and resilient closure are pulled off the second needle means, the second valve means is automatically permitted to close thereby preventing any further flow of blood until another of said blood container is coupled therewith.

7. Apparatus for collecting blood samples from a patient comprising:
   a housing;
   a first hollow, pointed needle extending forwardly from the housing and adapted for piercing the tissues of a patient and conducting blood therefrom;
   blood flow indicating means coupled with said first needle and adapted to provide a visual signal when the sample has penetrated a blood vessel;
   a chamber in the housing in fluid communication with a normally closed valve means adapted when closed to prevent any blood from flowing out of said chamber;
   a second hollow pointed needle extending rearwardly from the housing;
   said valve means adapted to be activated and shifted from the normally closed position to an open position to permit flow of blood from the patient to a blood sample container;
   said blood flow indicating means including control means to provide for a limited amount of blood to be directed to a predetermined location for indication purposes and to isolate the limited amount of blood and to prevent leakage beyond the desired location;
   the control means including at least one passageway in the housing in communication with the chamber and including sealing means therein so that upon accumulation of blood in the chamber and entrance into the passageway the sealing means will become activated to seal the passageway and prevent the blood from flowing therethrough beyond a predetermined location and the housing surrounding the passageway being of a material to permit visual observation of the blood flowing into and sealed in the passageway; and
   the sealing means in each passageway being a water expansible medium deposited on the surface surrounding the passageway so that upon contact with blood the water expansible material will expand and seal each passageway.

8. The invention in accordance with claim 7 wherein the water expansible material is in the form of a film.

9. The invention in accordance with claim 7 wherein the water expansible material is in the form of a powder.

10. The invention in accordance with claim 8 wherein the passageways are formed by providing channels in the film communicating between the atmosphere and the chamber and positioned so that upon leakage of blood from the chamber through the channels following the air therein to the atmosphere, the water expansible film will expand sealing the channels and trapping the blood intermediate the ends of the channels where it can be visually observed through the housing.

11. Apparatus for collecting blood samples from a patient comprising:
   A housing;
   a first hollow, pointed needle extending forwardly from the housing and adapted for piercing the tissues of a patient and conducting blood therefrom;
   blood flow indicating means coupled with said first needle and adapted to provide a visual signal when the sample has penetrated a blood vessel;
   a chamber in the housing in fluid communication with a normally closed valve means adapted when closed to prevent any blood from flowing out of said chamber;
   a second hollow pointed needle extending rearwardly from the housing;
   said valve means adapted to be activated and shifted from the normally closed position to an open position to permit flow of blood from the patient to a blood sample container;
   said blood flow indicating means including control means to provide for a limited amount of blood to be directed to a predetermined location for indication purposes and to isolate the limited amount of blood and to prevent leakage beyond the desired location;
   the valve means including a check valve coupled with said first needle and adapted to assume a first position to enable blood to flow out of the patient into a container and a second position to prevent any fluid from flowing back into the patient; and
   the check valve including a resilient member mounted in the housing and having a tubular shaped body portion with a pair of flaps extending rearwardly and inwardly therefrom so as to be normally in sealing engagement at their ends distal from the base portion, a central opening through the check valve normally closed at the rear end by means of the interengaging flaps and the flaps being adapted to be resiliently separated to permit blood to flow through the central opening of the check valve when the valve is subjected to a sufficient pressure differential in one direction, and when the pressure differential in the one direction is removed the resilient flaps will again come into engagement at their ends to seal the check valve.

12. The invention in accordance with claim 11 wherein the check valve is of a resilient self-sealing rubber material.

13. The method of transferring blood from a patient into a blood sample assembly and container which includes the steps of:
   Inserting a first sharp pointed hollow needle into a patient's blood vessel;
   conducting the patient's blood through said first needle and into a blood flow indicator;
   controlling the blood flow indicator so that a limited amount of blood is directed to a predetermined location for indication purposes and to isolate the limited amount of blood and prevent leakage beyond the desired location;
   pushing in the forward direction a partially evacuated blood collecting container with a resilient closure after the blood flow indicator has shown that the first needle has been successfully inserted in the patient's blood vessel, thereby causing a second hollow pointed needle to penetrate through the resilient closure, so that the blood container is operatively connected with said blood assembly, which has valve means located between a chamber of said blood sample assembly and the second hollow pointed needle;

transferring blood from the patient's blood vessel under the influence of the partial vacuum, through the first needle, through the chamber and valve means of the assembly, and through the second needle until the blood container is substantially filled without permitting the limited amount of isolated blood to accumulate with blood collected in the container; and removing the filled blood container in the backward direction thereby permitting the valve means to close.

14. The invention in accordance with claim 13 wherein the valve means is in the form of a check valve opened incident to the forward pushing of the blood container subjecting the assembly to the vacuum therein so as to permit blood to flow from the patient into the blood container while preventing fluid from flowing back into the patient by closing of the check valve upon a predetermined amount of reduction of vacuum.

15. The invention in accordance with claim 13 wherein a closure valve of elastomeric self-sealing material normally closes the opening in the exposed end of the second hollow pointed needle, the closure valve adapted to be automatically collapsed upon the use of pressure from the sample container being coupled with the second hollow pointed needle so as to expose opening in the end of the needle and permit the open ended needle to pass through the closure valve and enter the blood collecting container to subject the assembly to vacuum and permit blood to flow from the patient to the container, the closure valve normally automatically returning to the relaxed position upon removal of the container to once again close the opening in the end of the second needle, the opening and closing of the closure valve being repeatable automatically upon coupling of successive blood collecting containers in sequence.

* * * * *